US00PP36541P2

(12) United States Plant Patent
Erhart

(10) Patent No.: US PP36,541 P2
(45) Date of Patent: Mar. 11, 2025

(54) ***HIBISCUS* PLANT NAMED 'WALHIRHAP'**

(50) Latin Name: ***Hibiscus paramutabilis* x *syriacus***
Varietal Denomination: WALHIRHAP

(71) Applicant: Walberton Plants Limited, Walberton (GB)

(72) Inventor: Eva Erhart, Walberton (GB)

(73) Assignee: Walberton Plants Limited (GB)

( * ) Notice: Subject to any disclaimer, the term of this patent is extended or adjusted under 35 U.S.C. 154(b) by 0 days.

(21) Appl. No.: 18/670,980

(22) Filed: May 22, 2024

(51) Int. Cl.
*A01H 5/02* (2018.01)
*A01H 6/60* (2018.01)

(52) U.S. Cl.
USPC ..... Plt./257
CPC ..... *A01H 6/60* (2018.05)

(58) Field of Classification Search
USPC ..... Plt./257
CPC ..... A01H 5/02
See application file for complete search history.

(56) References Cited

PUBLICATIONS

CPVO Application Consultation Version 4.20.5 for 'WALHIRHAP'; Aug. 20, 2024; 2 pages.*

* cited by examiner

*Primary Examiner* — Kent L Bell
(74) *Attorney, Agent, or Firm* — Cassandra Bright

(57) ABSTRACT

A new and distinct cultivar of *Hibiscus* plant named 'WALHIRHAP' is disclosed, characterized by large, purple flowers with a deep red eye. Plants are observed winter-hardy to −10 degrees Celsius and heat tolerant to 40 Celsius without adverse effect. Growth habit is broadly upright and spreading more with age. The new variety is a *Hibiscus*, typically produced as an outdoor ornamental plant.

2 Drawing Sheets

Latin name of the genus and species: *Hibiscus paramutabilis* x *syriacus*.

Variety denomination: 'WALHIRHAP'.

BACKGROUND OF THE INVENTION

The new *Hibiscus* cultivar is a product of a planned breeding program by the inventor. *Hibiscus* 'WALHIRHAP' is the result of an open pollination of two unidentified *Hibiscus* varieties. Seed was bulk collected from various *Hibiscus* plants and parent variety information is not available. The open-pollination resulting in this new variety was made during 2014 at a nursery in Walberton, United Kingdom.

The new cultivar was found and selected by the inventor in a group of seedlings resulting from the 2014 open-pollination at the same nursery in Walberton, United Kingdom during 2015.

Asexual reproduction of the new cultivar 'WALHIRHAP' was first performed in July of 2019 in Walberton, United Kingdom, by softwood cuttings. Subsequent propagation has shown that the unique features of this cultivar are stable and reproduced true to type in successive generations.

SUMMARY OF THE INVENTION

The cultivar 'WALHIRHAP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WALHIRHAP'. These characteristics in combination distinguish 'WALHIRHAP' as a new and distinct *Hibiscus* cultivar:

1. Large purple flowers.
2. Broadly upright habit.
3. Winter hardiness to at least −10° C.

PARENT COMPARISONS

Details of the parent varieties are not available for comparisons.

COMMERCIAL COMPARISONS

Plants of 'WALHIRHAP' are similar in some horticultural characteristics to the variety *Hibiscus* 'WALHIROSMO', unpatented. The new variety, however, differs in the following:

1. Flowers of the new variety have petaloids, while flowers of this comparator do not.
2. Petals of the new variety overlap, while petals of this comparator do not overlap.
3. Flower color of the new variety is between RHS Purple-Red 72A and Purple N78A, while the flower color of this comparator is Purple N78B.

Plants of 'WALHIRHAP' are similar in some horticultural characteristics to the variety *Hibiscus* 'Woodbridge', unpatented. The new variety, however, differs in the following:

1. Flowers of the new variety are much larger than flowers of this comparator.
2. Petals of the new variety overlap, while petals of this comparator do not overlap.

3. Flowers of the new variety have petaloids, while flowers of this comparator do not.

BRIEF DESCRIPTION OF THE PHOTOGRAPHS

Figure 1:
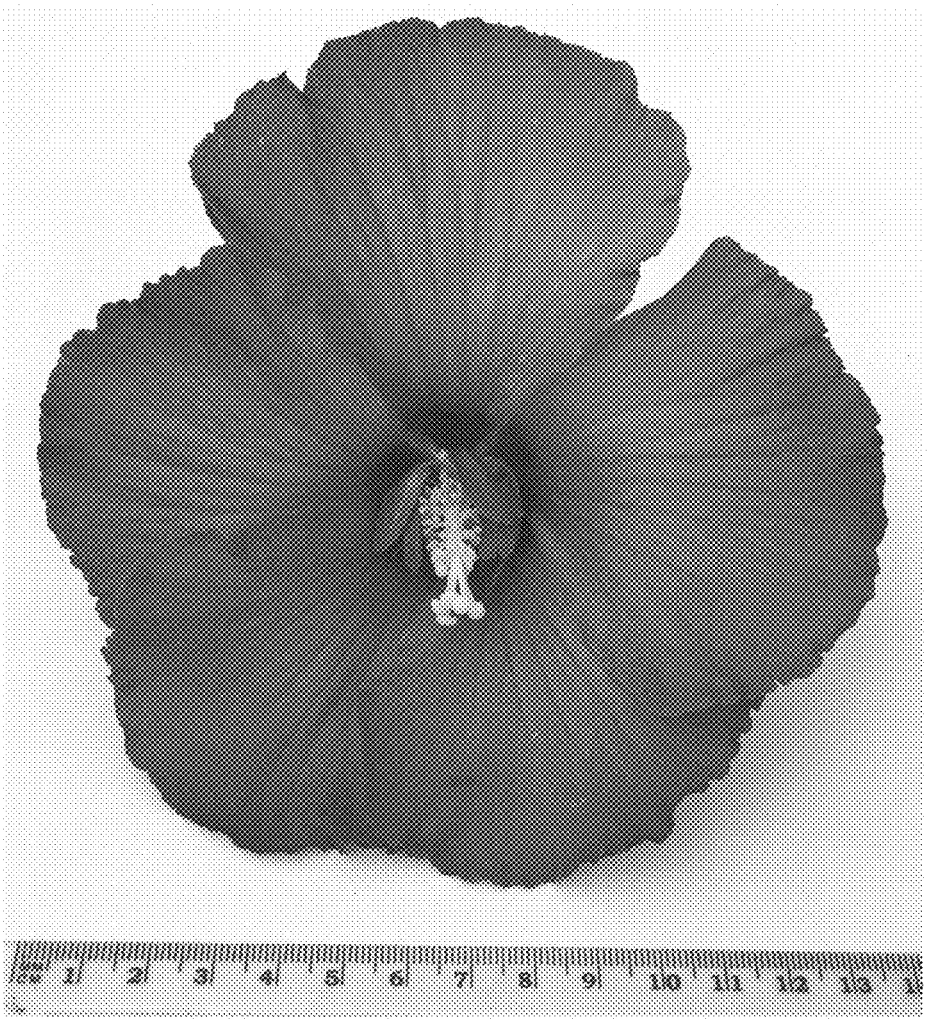

The accompanying drawing, FIG. 1 illustrates in full color a typical flower from a typical plant of 'WALHIRHAP' grown in an unheated glasshouse at a nursery in Walberton, United Kingdom. This plant producing this flower is approximately 3 years old.

Figure 2:
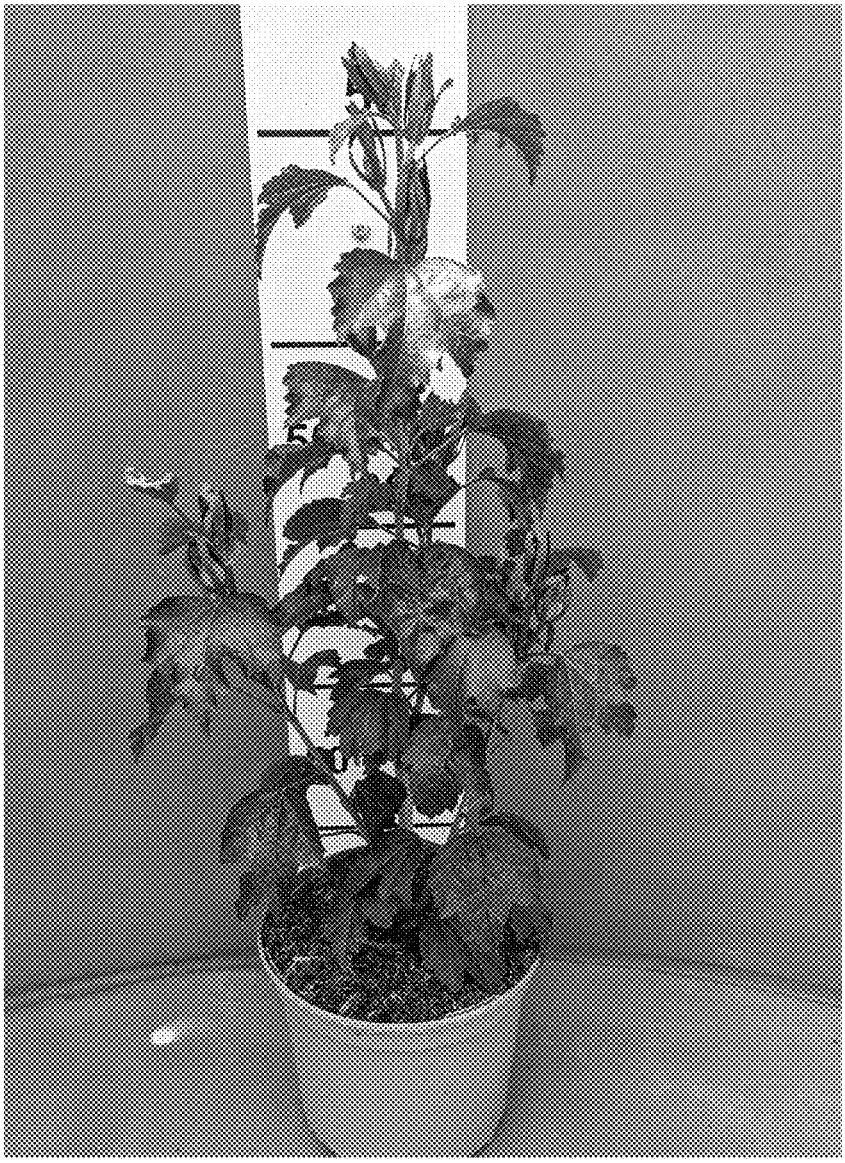

FIG. 2 illustrates a plant of about 1-year old during May, just before flowering begins.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe a 'WALHIRHAP' plant. This plant is approximately 3 years old, grown in a 6 liter container. Temperatures ranged from 0° C. to 33° C. during the day to −8° C. to 18° C. at night. No artificial light, photoperiodic treatments were given to the plants. Measurements and numerical values represent averages of typical plant types.

Botanical classification: *Hibiscus paramutabilis* x *syriacus* 'WALHIRHAP'.

PROPAGATION

Time to initiate roots: 20 to 24 days in summer; 14 to 18 weeks in winter at 0° C. to 33° C.

Time to produce a rooted cutting: About 6 to 7 weeks.

Root description: Fine, fibrous. Light tan and brown.

PLANT

Plant type: Deciduous flowering shrub.

Age of plant described: 3 years old.

Growth habit: Broadly upright, spreading slightly with age.

Growth rate: Moderate.

Height: 102 cm.

Plant spread: 78 cm.

Branching characteristics: Basal branching. Pinching required to promote lateral branching.

Primary lateral branches:

- *Quantity*.—Typically 15.
- *Length*.—48 to 55 cm.
- *Diameter*.—0.6 cm, tapering to 0.3 cm near apex.
- *Shape*.—Virgate, upright.
- *Strength*.—Stiff, strong.
- *Color*.—RHS Olive-Gray 197B.
- *Texture*.—Verruscose.

Internode length: 4.2 to 5.5 cm.

FOLIAGE

Leaf:

- *Arrangement*.—Alternate, spirally arranged, dextrorse; leaves held singly, very rarely in 2s or 3s at lower (older) nodes.
- *Quantity*.—14 to 19 per branch.
- *Average length*.—8.8 cm.
- *Average width*.—7.5 cm.
- *Shape of blade*.—Palmatifid, three-lobed.
- *Apex*.—Acute to obtuse.
- *Base*.—Subcuneate.
- *Margin*.—Sparsely serrate, lower third of each lobe more or less entire.
- *Texture of top surface*.—Areolate, very sparsely hispid.
- *Texture of bottom surface*.—Areolate, sparsely hispid.
- *Aspect*.—Petiole held 70° to 90° from stem.
- *Color*.—Young foliage upper side: RHS Yellow-Green 144A. Young foliage under side: RHS Yellow-Green 146B and 146C. Mature foliage upper side: RHS Green NN137A. Mature foliage under side: RHS Yellow-Green 147B. Autumn color upper side: RHS Yellow-Orange 19A. Autumn color under side: RHS Yellow-Orange 14C.
- *Venation*.—Type: Palmate. Venation color, upper side: RHS Yellow-Green 146B. Venation color, under side: RHS Yellow-Green 146C.
- *Petiole*.—Length: 4.6 cm. Diameter: 0.2 cm. Color: RHS Yellow-Green 146A. Texture: More or less glabrous, sparsely tomentose.

FLOWER

Natural flowering season: May to September in Walberton, UK.

Flower type and habit: Single, rotate, overlapping.

Flower shape: Trumpet-shaped. From above flowers are circular or slightly irregular circular.

Rate of flower opening: 2 to 3 days from bud dehiscence (cracking color) to fully opened flower.

Flowers and buds per plant: 16 to 24 flowers and buds per plant during peak summer flowering.

Flower longevity on plant: 2 to 3 days.

Persistence: Self-cleaning.

Fragrance: None.

Bud:

- *Shape*.—Ovate.
- *Length*.—3 cm.
- *Diameter*.—1.6 cm at widest.
- *Apex*.—Acute to attenuate.
- *Base*.—Rounded.
- *Texture*.—Scabrid to verrucose.
- *Color*.—RHS Yellow-Green 147C at base, 146C near apex.

Flower size:

- *Diameter*.—13.8 cm.
- *Depth*.—6 cm.

Petals:

- *Quantity*.—5.
- *Arrangement*.—Rotate.
- *Length*.—6.5 to 7 cm.
- *Width*.—6.5 to 7.2 cm at widest.
- *Shape*.—Orbicular to obovate.
- *Apex*.—Rounded.
- *Base*.—Obtuse.
- *Margin*.—Entire at the sides; undulate at the ends.
- *Texture, upper and lower surfaces*.—Glabrous, slightly shiny; more shiny on newly opened flowers, less shiny towards petal edges.
- *Color*.—Eye — size and feathering: Extends 15% to 20% of length of petal from petal base, low to moderate feathering on opening, moderate feathering when fully open. When opening, upper surface, main color: RHS Purple 77A and N78A. hen opening, upper surface, eye color: RHS Red-Purple 59A and 59B. When opening, lower surface: RHS Red-Purple N78A. Fully opened, upper surface, main color: RHS Red-Purple 72A and Purple N78A. Fully opened, upper surface, eye color: RHS Purple-Red 59A and 59B. Fully opened, lower surface: RHS Purple-Red 72A; veins White NN155A.

Petaloids:

*Quantity*.—Typically 8 to 10, can be as few as 6.

*Arrangement*.—Rotate; attached approximately 0.2 cm up stamen stalk.

*Length*.—1.4 to 3.6 cm.

*Width*.—0.6 to 1.3 cm.

*Shape*.—Obovate; whole petaloid is undulate to contorted and twisted.

*Apex*.—Mostly obtuse; sometimes bifid with two rounded lobes.

*Base*.—Attenuate.

*Margin*.—Entire at sides; apex crenate to crenulate.

*Texture, upper and lower surfaces*.—Glabrous, slightly shiny.

*Color*.—When opening, upper surface: RHS Purple-Red 72B. When opening, lower surface: RHS Purple N78A. Fully opened, upper surface: RHS Purple-Red 72B. Fully opened, lower surface: RHS Purple N78A.

Calyx sepals:

*Quantity*.—4 to 6, typically 5.

*Length*.—2.8 to 2.9 cm.

*Width*.—1.2 to 1.5 cm at widest part.

*Shape* (*overall*).—Broadly lanceolate, campanulate. Apex: Acute to attenuate. Base: Truncate, fused.

*Margin*.—Entire.

*Color*.—Upper and lower surfaces: RHS Yellow-Green 146B and 147B fading to 147D at base.

*Texture*.—Strigose to scabrid.

Epicalyx sepals:

*Quantity*.—5 or 6.

*Length*.—2.5 to 2.9 cm.

*Width*.—0.4 to 0.5 cm at widest part.

*Shape* (*overall*).—Linear-lanceolate, fused at base; campanulate overall.

*Apex*.—Acute to attenuate.

*Base*.—Truncate, fused.

*Margin*.—Entire.

*Color*.—RHS Yellow-Green 146A and 146B.

*Texture*.—Scabrid.

Peduncle:

*Length*.—2.7 cm.

*Diameter*.—0.3 to 0.35 cm.

*Angle*.—35° to 45° to the lateral branch.

*Strength*.—Strong, rigid.

*Texture*.—Scabrid to strigose.

*Color*.—RHS Yellow-Green 144A.

REPRODUCTIVE ORGANS

Stamen stalk:

*Length*.—2.7 cm.

*Diameter*.—0.4 cm at base, tapering to 0.25 cm near apex.

*Color*.—RHS White NN155D.

*Protruding beyond petals*.—Yes, in fully opened flowers.

Stamens:

*Quantity*.—Typically between 60 and 80.

*Arrangement on stalk*.—7 to 8 whorls.

*Filament color*.—RHS Yellow 2D.

Anthers:

*Shape*.—Globular.

*Length*.—Approximately 0.1 to 0.2 cm.

*Color*.—RHS White NN155D.

*Pollen*.—Color: RHS Yellow 12C and 12D. Quantity: Very little.

Pistil:

*Number*.—5.

*Length*.—0.6 cm.

*Style*.—Length: 0.4 cm. Color: RHS White 155B.

*Stigma*.—Shape: Oblately globular. Color: RHS White 155B. Ovary Color: RHS Yellow-Green 150D and 154D.

OTHER CHARACTERISTICS

Seeds: Not observed.

Disease/pest resistance: Neither resistance nor susceptibility to normal diseases and pests of *Hibiscus paramutabilis* x *Hibiscus syriacus* have been observed.

Temperature tolerance: Trialed without adverse effect at temperatures ranging −10° C. to 40° C.

What is claimed is:

1. A new and distinct cultivar of *Hibiscus* plant named 'WALHIRHAP' as herein illustrated and described.

* * * * *